United States Patent
Rothenberg

(10) Patent No.: US 12,419,903 B1
(45) Date of Patent: Sep. 23, 2025

(54) COMPOSITIONS AND METHODS OF TREATMENT FOR VARIOUS CONDITIONS USING HIGH-MOLECULAR WEIGHT HYALURONIC ACID

(71) Applicant: Embrient, Inc., San Diego, CA (US)

(72) Inventor: Barry E. Rothenberg, Del Mar, CA (US)

(73) Assignee: Embrient Inc., San Diego, CA (US)

( * ) Notice: Subject to any disclaimer, the term of this patent is extended or adjusted under 35 U.S.C. 154(b) by 0 days.

(21) Appl. No.: 18/482,891

(22) Filed: Oct. 8, 2023

Related U.S. Application Data

(63) Continuation-in-part of application No. 17/215,839, filed on Mar. 29, 2021, now Pat. No. 11,780,871.

(60) Provisional application No. 63/005,136, filed on Apr. 3, 2020.

(51) Int. Cl.
| | |
|---|---|
| *A61K 31/728* | (2006.01) |
| *A61K 35/19* | (2015.01) |
| *A61K 39/395* | (2006.01) |
| *A61K 45/06* | (2006.01) |

(52) U.S. Cl.
CPC ............ *A61K 31/728* (2013.01); *A61K 35/19* (2013.01); *A61K 39/3955* (2013.01); *A61K 45/06* (2013.01)

(58) Field of Classification Search
CPC ... A61K 31/728; A61K 35/19; A61K 39/3955
See application file for complete search history.

(56) References Cited

FOREIGN PATENT DOCUMENTS

WO  WO-2008140499 A2 * 11/2008 ........... A61K 31/728

OTHER PUBLICATIONS

Lu et al., Biosci. Rep., 2018, vol. 38(2): BSP20171555.*
Hirose et al., Proc. Nat'l. Acad. Sci. U.S.A., 2012, vol. 109(11):4263-4268.*
Andelid et al., BioMed Central, Respiratory Research, 2021, pp. 1-14.
Hellman et al., Journal of Biological Chemistry, 2020, 295(45), pp. 15418-15422. (Year: 2020).
Hirose et al., Proceedings of the National Academy of Sciences, 2012, vol. 109, No. 11, pp. 4263-4268.
Hu et al., Elsevier Journal, Biomedicine & Pharmacotherapy, 2020, pp. 1-11.
Knop et al., Elsevier Journal, Revista Brasileira de Reumatologia, 2016, pp. 152-164.
Szatmary et al., Adis, 2022, pp. 1251-1276.
Uchiyama et al., International Journal of Molecular Sciences, 2021, pp. 1-16.
Van Der Togt et al., Frontiers in Immunology, Hypothesis and Theory, 2023, pp. 1-5.
Zhong et al., Asian Journal of Pharmaceuticals Sciences, 2019, pp. 521-530.

* cited by examiner

*Primary Examiner* — Xiaozhen Xie
(74) *Attorney, Agent, or Firm* — Martin Fessenmaier; Umberg Zipser LLP

(57) ABSTRACT

A method of treatment is presented for alleviating and/or repairing damage associated with M1 macrophage-driven inflammation through administration of high molecular weight hyaluronic acid (HMW-HA), optionally in combination with platelet-rich plasma (PRP) and/or anti-Stabilin-2 antibodies. Preferred embodiments are formulated for parenteral administration and either directly or indirectly suppress M1 macrophage activity, and/or directly indirectly promote M2 macrophage polarization.

11 Claims, No Drawings

COMPOSITIONS AND METHODS OF TREATMENT FOR VARIOUS CONDITIONS USING HIGH-MOLECULAR WEIGHT HYALURONIC ACID

This application is a continuation-in-part of U.S. patent application Ser. No. 17/215,839, filed Mar. 29, 2021 (now U.S. Pat. No. 11,780,871), which claims priority to U.S. Provisional Patent Application No. 63/005,136, filed Apr. 3, 2020, each of which are incorporated by reference herein.

FIELD OF THE INVENTION

The field of the invention is a method of treatment for M1 macrophage driven inflammation, especially as it relates to the role of hyaluronic acid (HMW-HA) and/or platelet-rich plasma (PRP) and/or anti-Stabilin-2 antibody in direct and/or indirect suppression of M1 macrophage polarization, as well as direct and/or indirect promotion of M2 macrophage polarization.

BACKGROUND OF THE INVENTION

The background description includes information that may be useful in understanding the present disclosure. It is not an admission that any of the information provided herein is prior art or relevant to the presently claimed invention, or that any publication specifically or implicitly referenced is prior art.

All publications and patent applications herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply.

After several noteworthy coronavirus outbreaks in the recent years, including SARS and MERS, SARS-CoV-2 is yet another example of a serious infectious disease precipitated by a member of the coronavirus family. While diagnostic tests have become available in relatively short time, numerous attempts to treat or mitigate the disease have so far not had significant success. Most typically, patients with severe symptoms are treated to maintain respiration/blood oxygenation, and supportive treatment is provided to reduce or prevent multi-organ damage or failure. Despite such interventions, the mortality rate is significant, particularly in elderly, immune compromised individuals, and individuals with other underlying conditions, including heart disease, lung disease, or diabetes.

Indeed, a clear understanding of causative factors contributing to the increased severity of COVID-19 in patients with underlying medical conditions seems to be largely absent. This lack of understanding is likely contributing to the inability to identify therapeutic compounds that are effective and safe in reducing damaging pathologies observed in this disease. There is an immediate need to identify therapeutic compounds and develop delivery protocols that will reduce severity of the pathology without appreciably altering the protective acquired immune response.

Thus, even though various methods of addressing symptoms in patients with COVID-19 are known in the art, all or almost all of them suffer from various disadvantages. Consequently, there is a need to provide improved compositions and methods that provide therapeutic effect, that reduce or prevent an exacerbated immune response and/or cytokine storm. Indeed, dampening an escalating immune response would reduce, or even avoid the need for ventilators in COVID-19 patients.

Viewed from a different perspective, there is a need to reduce the severity of an escalating immune response that would otherwise lead to significant tissue and organ damage, particularly in individuals that have underlying health conditions that render such individuals susceptible to such damage. For example, acute pancreatitis is typically accompanied by a marked imbalance between proinflammatory and anti-inflammatory responses, which in turn often leads to a progression of the acute pancreatitis resulting in localized tissue destruction and distant organ damage. (Makhija R, Kingsnorth AN. Cytokine storm in acute pancreatitis. *J Hepatobiliary Pancreat at Surg.* 2002; 9(4):401-10. doi: 10.1007/s005340200049. PMID: 12483260). In the acute pancreatitis setting, the imbalance towards inflammatory response and the damage that follows, poses a challenge that has yet to be met.

Hyaluronic acid is an anionic, non-sulfated glycosaminoglycan that is widely distributed throughout the human body. For example, hyaluronic acid is found in the extracellular matrix, articular cartilage and synovial fluid, and skin. Hyaluronic acid has also found use in various therapeutic applications such as dermal fillers and topical cosmetics. Moreover, specific mixtures of high- and low-molecular weight with different rheologies were described in U.S. Pat. No. 9,029,347 to form a protective and adhesive barrier in intestinal tissues in the treatment of inflammatory bowel disease. In a further example, WO 2008/140499, discloses use of substantial quantities of high-molecular weight hyaluronic acid (HMW-HA) in the circulatory system to treat sepsis. Here, between about 5% and 20% of the circulating blood volume of a subject HMW-HA is transfused to the subject in an apparent attempt to prevent low-molecular weight binding to cell surfaces and to counteract hypotensive state.

Thus, even though various methods are known in the art to use hyaluronic acid to treat and prevent various conditions, all or almost all of them suffer from various disadvantages. Consequently, there is still a need to provide improved compositions and methods that reduce or prevent an exacerbated immune response, and particularly an inappropriate immune response that is characterized by excessive presence and activity of M1 macrophages and, in so doing, avoid or reduce organ and systemic damage.

SUMMARY OF THE INVENTION

The inventor has now discovered compositions and methods for treatment of acute pancreatitis or other conditions related to an inappropriate and/or exacerbated immune response to M1 macrophage-driven inflammation. Damage resulting therefrom can be reduced or even entirely avoided by providing one or more therapeutic agents such as high molecular weight hyaluronic acid (HMW-HA), optionally in combination with platelet-rich plasma (PRP) and/or anti-Stabilin-2 antibodies, through parenteral administration.

In one aspect of the inventive subject matter, the inventor contemplates a method of treatment of acute pancreatitis that includes parenteral administration to a subject diagnosed with or suspected to have acute pancreatitis, a composition of HMW-HA in an amount effective to treat the acute pancreatitis.

In some embodiments, the parenteral administration comprises injection of the HMW-HA into or proximal to a treatment area. Additionally, the parenteral administration comprises implantation of a device or composition that includes the HMW-HA into or proximal to a treatment area. Consequently, the effective amount is an amount that induces M2 macrophage polarization and/or suppresses M1 macrophage activity. Furthermore, the effective amount is an amount that reduces elevated M1 macrophage levels and/or abrogates a cytokine storm.

In further embodiments, the inventive subject matter further comprises a step of administering platelet-rich plasma (PRP) and/or an anti-Stabilin-2 antibody. Moreover, the inventive composition includes the PRP and/or the anti-Stabilin-2 antibody. Most typically, but not necessarily, the HMW-HA has a molecular weight of between 1,000 and 3,000 kDa, and parenteral administration of the composition is performed between 0 and 7 days of confirmation of the acute pancreatitis. Nonetheless, the composition further includes an anti-inflammatory drug, an antibiotic, and/or an antineoplastic compound.

Viewed from a different perspective, the inventor additionally contemplates a method of treatment of a M1 macrophage-drive inflammatory condition in a subject that includes diagnosing that the inflammatory condition is an M1 macrophage-driven inflammatory condition, then upon diagnosis, parenterally administering to the subject a composition comprising HMW-HA, and optionally further including PRP and/or an anti-Stabilin-2 antibody, wherein the composition is administered in an amount that induces M2 macrophage polarization and/or suppresses M1 macrophage activity.

Preferably, the M1 macrophage-drive inflammatory condition is a cytokine "storm," an autoimmune disease, an acute inflammatory disorder, a chronic inflammatory disorder, atherosclerosis, or periodontitis. Moreover, the diagnosing comprises ascertaining in the subject a clinically elevated M1 macrophage cell count or reference to a publication establishing that the condition is an M1 macrophage-driven inflammatory condition.

Most typically, but not necessarily, parenteral administration comprises injection of the HMW-HA into or proximal to a treatment area. In addition, parenteral administration comprises implantation of a device or composition including the HMW-HA into or proximal to a treatment area. Furthermore, parenteral administration of the composition is performed between 0 and 7 days of the step of diagnosing, and parenteral administration is repeated at least three time over a treatment period.

Additionally viewed from a different perspective, the inventor also contemplates a composition that includes a combination of HMW-HA with (a) PRP and/or (b) an anti-Stabilin-2 antibody, wherein the HMW-HA is present in an amount effective to induce, upon administration to a treatment area, M2 macrophage polarization in the treatment area and/or suppress M1 macrophage activity in the treatment area, and wherein the combination is formulated for injection or implantation.

In some embodiments, the composition comprises the PRP and the anti-Stabilin-2 antibody. In still further contemplated embodiments, the composition is formulated as a dermal filler.

Various objects, features, aspects, and advantages will become more apparent from the following detailed description of preferred embodiments.

DETAILED DESCRIPTION

The inventor now contemplates various compositions and methods of treatment of acute pancreatitis and other M1 macrophage-driven inflammatory conditions through parenteral administration of high molecular weight hyaluronic acid (HMW-HA), and optionally further including platelet-rich plasma (PRP) and/or an anti-Stabilin-2 antibody, to induce M2 macrophage polarization and/or suppress M1 macrophage activity.

In one aspect of the inventive subject matter, the inventor has now discovered certain mechanisms that cause severe pathology prior to and during the SARS-CoV-2 infection and aligns the observed molecular and cellular events with the disease timeline. More particularly, the inventor postulates that the 'ground glass' X-ray that is seen in as few as 3-4 days after onset of COVID-19 patients symptoms, is caused by prior long-term chronic stimulation of pro-inflammatory M1 macrophages and the resulting new recruitment of innate immune cells (e.g., neutrophils). Between days 10 and 12 of the infection, viral antigen specific IgG appears and attaches to the surface Fc receptor of the macrophages, thus arming the cytokine rich innate immune cells that are already present in an excessive quantity (e.g., due to smoking, aerosol-induced lung damage, etc.) relative to a healthy patient without chronic stimulation of pro-inflammatory M1 macrophages. Once these cells contact the viral antigens, they immediately release cytokines, resulting in a destructive cytokine storm. Consequently, one significant aspect of contemplated COVID-19 treatments is to dampen this initial inflammatory response without interfering with the protective T and B cell acquired immune response phase.

In this context it is important to recognize that the damage to other organs in late stages of COVID-19 appears to be the result of a breakdown of the hyaluronic acid (HA) physical barrier protecting alveoli cell wall fibrous structural components, including elastin fibers. When this structure is damaged, the alveoli cell walls become leaky allowing for the rapid release of armed neutrophils, which will then precipitate further damage outside the lung. It should also be appreciated that most of the cellular and metabolic factors associated with increased risk for prolonged and severe complications from COVID-19 have common metabolic and immunologic characteristics. Specifically, the similarities are: (1) polarization of M1 and M2 macrophages of the innate immune system; and (2) decreased intracellular $NAD^+$ levels. Notably, both of these characteristics accompany inflammation.

Based on the above considerations and further observations below, the inventor discovered that there are various readily available compounds/compositions to address these characteristics: (1) commercially available nutritional supplements that have been shown to increase cellular $NAD^+$ levels; and (2) an inhalable aerosol form of hyaluronic acid (HA) (an FDA approved drug) that has successfully been used to treat cystic fibrosis. Moreover, an aerosol form of high-molecular weight (HMW)-HA inhaled twice a day has been shown by others to play a protective role in reducing elastin degradation. Advantageously, such agents are inexpensive, safe, readily available, and are simple to administer. In particular, one or more agents may be given to an individual to increase levels of nicotinamide adenine dinucleotide ($NAD^+$) in a subject, which may be done prophylactically or upon diagnosis of SARS-CoV-2 infection; and high molecular weight-hyaluronic acid (HMW-HA) may be administered upon a positive test for the SARS-CoV-2 but prior to an escalating immune response (e.g., immediately after diagnosis). The following provides further details and aspects of contemplated methods. However, while the present disclosure generally refers to SARS-CoV-2, infections with respiratory viruses other than coronaviruses (e.g., rhinoviruses, adenoviruses, respiratory syncytial viruses, influenza viruses (including avian influenza viruses such as H5N1 bird flu), parainfluenza viruses, parvoviruses, etc. are expressly contemplated in conjunction with the teachings presented herein, particularly where such viral infections lead to acute respiratory distress syndrome (ARDS).

Prophylactic Increase in NAD$^+$ Levels

NAD$^+$ is a naturally occurring coenzyme synthesized in all cells. It is found in two forms: either oxidized (NAD$^+$) or reduced (NADH). The NAD$^+$/NADH ratio is tightly controlled in the body, and its imbalance can lead to clinical pathologies. Notably, all of the underlying risk factors for COVID-19 as noted below are associated with lowered levels of intracellular NAD$^+$. For example, the age-associated decline of NAD$^+$ levels in many tissues is the result of cellular senescence and increased inflammation. In addition, others have shown that reduced levels of NAD$^+$ typically accompanies increased polarization of inflammatory CD38$^+$ M1 macrophages. Thus, it should be recognized that NAD$^+$ supplements (and other forms of NAD$^+$ delivery to an individual) are recommended to be taken prophylactically by all individuals with underlying inflammatory conditions. This could reduce the risk of experiencing excessive inflammation of the lungs and other organs if they contract COVID-19.

Some of the underlying conditions that put COVID-19 patients at a higher risk for severe pathology include advanced age (e.g., >60 yr) and patients diagnosed or suspected to have diabetes, asthma, hypertension (patients on high blood pressure medications, e.g. ACE2 inhibitors and Ca$^+$ channel blockers), atherosclerosis, rheumatoid arthritis, pulmonary disease (e.g., COPD and idiopathic pulmonary fibrosis (IPF), particle sizes equal to or less than 2.5 µm). This group includes smokers (including smokers of marijuana and inhaled recreational drugs, and possibly vapers), and individuals exposed to diesel exhaust and air pollution (e.g., industries which produce an abundance of air borne 2.5 µm particles as with coal fired power plants).

There are several distinct populations of cells residing in the lungs that belong to the innate arm of the immune system. For brevity, this discussion will focus on the coordinated inflammatory effects of M1 and M2 macrophages. Pro-inflammatory M1 macrophages are derived from M2 macrophages and are responsible for killing pathogens. While the anti-inflammatory M2 macrophages heal or repair tissues, the M2 cells also play an anti-tumor phagocytic role. M1/M2 macrophages are part of the innate immune system and have a central role in activating T and B cell adaptive immune responses. Polarization of M1 and M2 macrophages is a key component in the progression of serious pulmonary pathology. Besides virus-induced lytic damage, rapid viral replication induces M1 polarization and inflammation, which are the two main causes of lung damage. Healing M2 macrophages produce the immunosuppressive cytokine IL-10, which down-regulates the production of various M1 pro-inflammatory cytokines such as IFNγ, TNFα, IL-1β and IL-12.

Administration of HMW-HA Upon COVID-19 Diagnosis

Hyaluronic acid (HA) is a disaccharide polymer made up of the repeating D-glucuronic acid and N-acetylglucosamine units. HA and elastin fibers play a critical role in maintaining the lung matrix structure. This is especially true in the alveolar cells, where HA surrounds and protects elastin fibers. In this context, it should be especially appreciated that HA polymers have multiple effects depending on size. More particularly, HA polymers with a molecular weight of between 1000 kDa and 3000 kDa are effective in polarizing M2 macrophages, increasing the M2 macrophage production of IL-10 and suppressing the output of damaging cytokines produced by M1 cells. High molecular weight HA (HMW-HA greater >1000 kDa) has been used to reverse pulmonary inflammation and damage in particle induced (size 2.5 µm) lung inflammation in a mouse model. Furthermore, an inhalable aerosol form of high molecular weight hyaluronic acid (HMW-HA) has been demonstrated to be safe and effective in slowing the progression of Chronic Obstructive Pulmonary Disease (COPD) in humans. COPD includes bronchitis and emphysema. There are multiple contributing factors to COPD such as farmer's lung resulting from inhalation of plant derived mold. Other reports show a clear association with small sized particles <2.5 µm produced by smoking, flour dust, and coal powered energy plants.

When acute viral-induced inflammatory activation continues, it will lead to excess lymphocyte pulmonary recruitment, including polarization of M1 cells and neutrophils, another distinct cell type of the innate immune system. Recruitment of these cell types leads to increased inflammatory cytokine production and release. Unfortunately, this process initiates large-scale enzymatic fragmentation of HMW-HA, resulting in accumulation of low molecular weight inflammatory HA, which in turn further stimulates activity of M2 macrophages and neutrophils. The outcome of this cellular and molecular process is severe pulmonary damage and ultimately death. Furthermore, ventilator-induced lung injury may be an added physical concern in HMW-HA degradation and subsequent inflammatory response.

It should be particularly appreciated that the biochemical activity of HA is dependent on polymer length. Length influences cell receptor binding and altered gene expression: HMW-HA is known to be the ligand for the M2 cell surface receptor CD44. Binding of HMW-HA to CD44 stimulates the production of an anti-inflammatory cytokine, IL-10. Shorter length HA polymers have the opposite effect, by suppressing IL-10 production. HMW-HA has been previously demonstrated to be effective when administered to cystic fibrosis patients twice a day for 28 days and did not have reported adverse effects.

In addition, it should be noted that the timing of HMW-HA intervention is of significance as earlier administration of HMW-HA improves the odds of reducing buildup of large numbers of inflammatory cells, resulting in reduced pulmonary damage and limiting the need for ventilation. As will be readily appreciated, HMW-HA is therefore not an antiviral drug for treatment of COVID-19, but rather a stop-gap measure intended to reduce the projected pressures on healthcare systems (e.g., supportive treatments, ventilation, etc.).

Viewed from a different perspective, the rapid pulmonary injury seen between days 10-14 in COVID-19 patients may be the result of earlier M1 recruitment of various cell types of the innate immune system. These include natural killer cells, neutrophils, and increased polarization of M1 macrophages. The switch from IgM to IgG antibody production around day 10 of the infection would allow for the anti-viral antigen specific IgG arming of the rapidly accumulating innate effector cells. This simple explanation accounts for the enhanced release of destructive cytokines, which explains the rapid destruction (sometimes in as little as 4 hours) of pulmonary tissue as seen in CAT-scans of COVID-19 patients. The model is testable by collecting lavage samples prior to and during HMW-HA administration and identifying accumulating numbers of each innate cell type through the entire course of treatment and recovery.

Predisposing Genetic Factors

The inventor also observed that there may be genetic factors that predispose COVID-19 patients for severe pulmonary pathology. In the 2003 SARS-CoV epidemic, Taiwanese researchers noticed a significant number of SARS-CoV patients with severe pulmonary disease that did not seem to have any underlying condition, such as age or smoking, which would have put them at higher risk for disease pathology. They therefore screened this population for HLA class 1 association. Their data identified two HLA alleles that were significantly elevated in this patient group. They were HLA-B*46:01 and HLA-C*15:01. HLA-B*46:01 was formed by a gene conversion event between HLA-B*15:01 and HLA-C*01:0. With this knowledge they immediately tested front line healthcare workers and identified individuals expressing these alleles. Once identified, they were removed from direct contact with COVID-19 patients and exposure to SARS-CoV.

Exemplary Compositions And Methods

In view of the above, the inventor contemplates that all compositions that increase $NAD^+$ levels are deemed suitable for use herein. Such $NAD^+$ increase will typically be achieved by administering a prodrug form or precursor that can be metabolized to $NAD^+$. Most preferably, such compositions include nutraceutical and pharmaceutical compositions, which may be administered in any suitable routs, and most preferably via oral or parenteral route. For example, suitable supplements include niacin, nicotinamide riboside, NAD per se, and further compounds and precursors as described, for example, in WO2018030389, WO201924298, US20190382436, WO2005115428, US20170266218, WO2019053518, and U.S. Ser. No. 10/392,414, all incorporated by reference herein.

Most typically, the compositions that increase $NAD^+$ levels will be administered in known and generally acceptable dosage level known for the composition. Therefore, suitable dosage levels will typically be between 10-100 mg/day, or between 100-200 mg/day, or between 200-600 mg/day, or between 600-1,000 mg/day, and even higher. Administration is preferably performed daily, or at least twice a week, or at least weekly, etc., preferably for a period of at least one week, or at least two weeks, or at least one month, or at least 1 year where administration is prophylactically. On the other hand, where the administration commences at the time of COVID-19 diagnosis or determination of infection with SARS-CoV-2, administration is at least every other day, or daily, or at least twice daily, or even continuously over at least several hours in case of infusion. In such cases, the daily dosage may be higher, such as between 200-400 mg/day, or between 400-800 mg/day, or between 800-1,500 mg/day, and even higher.

With respect to suitable HA formulations it is generally preferred that the HA is a HMW-HA, typically with a molecular weight of between 1,000 kDa and 3,000 kDa. Moreover, the HMW-HA may be crosslinked (e.g., via urea), branched, or linear. While not limiting to the inventive subject matter, the HMW-HA is administered directly into the lung, preferably in an aerosolized form and optionally on a carrier. On the other hand, the HMW-HA may also be administered to the lung via injection or lavage as best suitable or tolerated by the patient. With respect to suitable dosages, it is generally preferred that the HMW-HA administration 100 mg to 300 mg per dose, or between 300 mg to 600 mg per dose, or between 600 mg to 1,000 mg per dose, or between 1,000 mg to 3,000 mg per dose, or between 3,000 mg to 5,000 mg per dose, or even higher. The person of ordinary skill in the art will be readily able to determine the proper dosage based on known uses of inhalable HMW-HA and severity of the condition of the patient. In addition, it is also contemplated that inhibitors of hyaluronidase may be administered to the patient to reduce the degradation of HMW-HA. For example, contemplated inhibitors include L-Ascorbic Acid 6-Hexadecanoate, high molecular mass poly (styrene-4-sulfonate), fenoprofen, gossypol, sodium aurothiomalate, glycerrhizic acid, fatty acids, plant-derived compounds, heparin, and O-sulfated HA (sHA).

It is further contemplated that the HMW-HA and $NAD^+$ may be co-administered or administered separately (e.g., sequentially), and the mode of co-administration is not deemed critical at this juncture. Indeed, sole administration of HMW-HA may be performed, particularly where levels of $NAD^+$ are deemed within physiological concentrations. However, it is generally preferred that the administration of HMW-HA is performed upon confirmation of SARS-CoV-2 infection, and most typically before onset of symptoms or before escalation of the immune response. Therefore, in most cases, administration will commence within one day, or within two days, or within three-five days, or within five to nine days, or within six to twelve days from the date of confirmation of SARS-CoV-2 infection. Viewed from a different perspective, HMW-HA (and NAD) administration will be prior to development of ARDS or cytokine storm.

In still further contemplated aspects, it should also be noted that the compositions presented herein can be employed to treat long-haul individuals that exhibit ongoing symptoms or that exhibit post initial recovery (and possibly viral clearance) one or more long-haul symptoms, including fatigue, shortness of breath, difficulty breathing, blood clots, muscle or body aches, and/or difficulty concentrating. Most typically treatment may commence (or continue beyond) at least 14 days after confirmation of the infection to thereby treat long-haul symptoms, and may be continued for at least 7 days, or at least 14 days, or at least one month, or even longer. Still further, it is contemplated that HMW-HA can be administered by injection (e.g., into a joint such as knee or shoulder) to so reduce inflammation via modulation of the macrophage population.

Treatment or Prevention of Acute Pancreatitis and/or Other M1 Macrophage-Driven Inflammatory Conditions In another aspect of the inventive subject matter, the inventor has discovered a method of treatment of acute pancreatitis that includes parenteral administration to a subject, diagnosed with or suspected to have acute pancreatitis, a composition comprising high molecular weight hyaluronic acid (HMW-HA) in an amount effective to treat the acute pancreatitis. In this context, it should be noted that development and progression/exacerbation of acute pancreatitis is driven by M1 macrophage polarization in the presence of elevated levels of pro-inflammatory cytokines (and especially TNF-alpha, IL-1, IL-6, IL-8 and/or IL-12), which in many cases will lead to a run-away pro-inflammatory response that ultimately leads to cytokine storm and often serious organ damage or even death.

Viewed from a different perspective, the inventor therefore also contemplates a method of treatment of an M1 macrophage-driven inflammatory condition in a subject that includes diagnosing that the inflammatory condition is an M1 macrophage-driven inflammatory condition, and upon diagnosis, parenterally administering to the subject a composition comprising HMW-HA that may optionally further include platelet-rich plasma (PRP) and/or an anti-Stabilin-2 antibody. Most typically, the composition is administered in an amount that induces M2 macrophage polarization and/or suppresses M1 macrophage activity/proliferation.

As will be readily appreciated, the diagnosis of an M1 macrophage-driven inflammatory condition will typically include an analytic method to ascertain in the subject a clinically elevated M1 macrophage cell count. For example, such elevated count can be established by various FACS methods using whole blood, obtaining of tissue samples, staining, and light microscopy, etc. In considering the levels of a subject's M1 macrophage cell count, a clinically elevated M1 macrophage cell count is one where the subject has at least 5% higher, at least 10% higher, at least 25% higher, at least 50% higher, at least 75% higher, or at least 100% higher M1 macrophage cell count as compared to a clinical normal reference value. Most commonly, such elevated M1 count is also accompanied by a clinically reduced M2 cell count. A clinically reduced M2 macrophage cell count is typically one where the subject has at least 5% lower, at least 10% lower, at least 25% lower, at least 50% lower, at least 75% lower, or at least 100% lower M2 macrophage cell count as compared to a clinically normal reference value. Such elevated M1 cells count (and reduced M2 cell count) will generally be observed along with clinically elevated pro-inflammatory cytokine levels in the diagnosis of an M1 macrophage-driven inflammatory condition. Of course, and depending on the severity and/or progression of the condition, it should be appreciated that these metrics may be observed systemically or locally (e.g., at the site of local inflammation such as the pancreas). Alternatively, an M1 macrophage-driven inflammatory condition may also be diagnosed by reference to publication that establishes that the condition is an M1 macrophage-driven inflammatory condition.

Consequently, it should be recognized that contemplated composition and methods of treatment are not only suitable for treatment of acute pancreatitis but may also be used in the treatment or prevention of COVID induced heart attack or stroke (which is characterized by elevated levels of foam cells (lipid-laden macrophages)) and atherosclerosis. Here, oral or systemic administration of HMW-HA may indeed control circulating M1 macrophages, and particularly lipid-laden macrophages, which in turn will reduce intraarterial plaque size (and so reduce the risk of heart attack and stroke).

Moreover, contemplated composition and methods of treatment may also be implemented in the treatment of acute lung injury, influenza, autoimmune disease, acute inflammatory disease, chronic inflammatory disease, and/or periodontitis, all of which can be categorized as an M1 macrophage-driven inflammatory condition. For example, it should be appreciated that in chronic bronchitis (and most typically chronic bronchitis associated with COPD), lung macrophages drive mucus production and steroid-resistant inflammation. Notably, it has been shown that macrophages from chronic bronchitis patients were chronically activated and resistant to steroid treatment (see e.g., *Respir Res* (2021) 22:172). As such, an urgent need exists to treat this condition, and the inventor contemplates that pulmonary administration of HMW-HA as described above will reduce, if not entirely abrogate M1 hyperactivity and stimulate M2 polarization, leading to significant improvement in chronic bronchitis. In further contemplated embodiments, compositions and methods according to the inventive subject matter may also be used in the improvement or enhancement of lifespan and/or health span. In still further embodiments, the composition is formulated as a dermal filler for injection into the intradermal or subdermal layers for treatment or prevention of deep wrinkles, grooves, volume loss, limp skin, and/or collagen reduction. In that context, it should be particularly appreciated that when combined with platelet rich plasma (PRP) and/or anti-stabilin 2 antibodies, the benefits to the skin may be significantly reduced inflammation and slow down, at least visually, the effects of "skin aging," the formation of wrinkles.

Viewed from another perspective, contemplated compositions will be formulated for oral, parenteral, and even topical administration, wherein the HMW-HA is present in an amount effective to induce, upon administration to a treatment area, M2 macrophage polarization in the treatment area and/or suppress M1 macrophage activity in the treatment area. Most typically, the combination is formulated for injection or implantation. In addition, it should be appreciated that contemplated compositions may additionally comprise PRP and/or an anti-Stabilin-2 antibody. In this context, it should be appreciated that the PRP is typically obtained from the same subject that receives the HMW-HA and PRP. While not wishing to be bound by any theory or hypothesis, it is contemplated that the PRP will provide an additional anti-inflammatory component (typically with a longer acting effect) that may increase the therapeutic effect of the HMW-HA, in some cases possibly even synergistically. With regard to the anti-stabilin-2 antibody it is contemplated that the antibody will bind to stabilin-2, which is a hyaluronan receptor that mediates hyaluronan endocytosis. Consequently, anti-stabilin-2 antibody are believed to maintain higher concentrations of HMW-HA for a longer time period.

In this context, it should be appreciated that platelet-rich-plasma (PRP) is a concentrated extract of platelets from autologous blood. PRP is rich in various growth factors and, as a result, can promote tissue regeneration and angiogenesis. Among the various growth factors are platelet-derived growth factor (PDGF), interleukin-1 receptor antagonist (IL-1RA), soluble receptor of tumor necrosis factor α (TNH-RI), transforming growth factor β (TGF-β), platelet factor 4 (PF4), vasculare endothelial growth factor (VEGF), epidermal growth factor (EGF), insulin-like growth factor (IGF), osterocalcin (Oc), osteonectin (On), fibrinogen, vitronectin, fibronectin, and thrombospondin-1 (TSP-1). As such, it is contemplated that at least some of the aforementioned growth factors will play a role in eliminating the imbalance of cytokines in the target area and/or in synthesizing hyaluronic acid. Furthermore, PRP reduces the expression of M1 macrophage markers, thereby suppressing M1 macrophage polarization, and promoting polarization of M1 macrophages to M2 macrophages. In some embodiments, the platelet concentrate is acquired by single centrifugation to obtain plasma rich in growth factors. In other embodiments, the platelet concentrate is acquired by double centrifugation to obtain higher leukocyte concentrations. In addition to PRP, it is further contemplated that various other cell-containing preparations are deemed suitable in addition to or as substitute for PRP, and particularly cells that express CD44 on the cell surface (e.g., mast cells) and that can produce IL-10.

As mentioned herein, hyaluronic acid (HA) polymers with a molecular weight of between 1000 kDa and 3000 kDa are deemed to be effective in polarizing M2 macrophages, increasing the M2 macrophage production of IL-10, and suppressing the output of damaging cytokines produced by M1 cells. However, HA is rapidly cleared from the bloodstream due to the activity of the scavenger receptor Stabilin-2 (Stab2). The Stab2 receptor, which is located in the liver and spleen, binds to and eliminates HA from the circulatory system. As a result, the quick removal of HA from circulation temporally limits the ability of HA to polarize M2 macrophages and suppress damage caused by M1 macrophages; thereby decreasing the effectiveness of circulating HA. Thus, the inventor contemplates that to prevent, or at least substantially reduce, the clearance of HA from the bloodstream as caused by Stab2, an anti-Stabilin-2 antibody can be administered. By inhibiting Stab2 function, levels of HA can remain elevated, or at least maintained, in a manner that permits prolonged functioning of the HA in circulation or at the point of administration or implantation.

Moreover, it should be appreciated that injection or implantation of the HMW-HA into or proximal to a treatment area may use various formulations, including infusion or injection of a liquid formulation, injection of a gel (e.g., hydrogel), implantation of a HMW-HA containing pharmaceutically acceptable carrier, etc. As noted above, such formulations may further include platelet-rich plasma (PRP) and/or an anti-Stabilin-2 antibody in conjunction with the HMW-HA. Alternatively, the PRP and/or the anti-Stabilin-2 antibody may be administered separately using the same or a different route of administration.

Consequently, injection or implantation into the treatment area includes the placement of HMW-HA in the immediate vicinity of the treatment area for direct treatment of a condition. Whereas injection or implantation proximal to a treatment area includes nearby placement of HMW-HA to the treatment area and/or systemic circulation of the HMW-HA, for indirect treatment of the condition.

Furthermore, it should also be appreciated that implantation of the HMW-HA into or proximal to a treatment area may include use of a device or composition that comprises a bio-erodible polymer, phase change polymer, biodegradable polymer, hydrogel, and/or stent. Most typically, but not necessarily, the implant is a radiopaque, opaque, firm, soft, pliable, or flexible unit that is impregnated or constructed with HMW-HA. In some embodiments, the release of HMW-HA upon implantation is contemplated to be immediate, intermittent, or prolonged. Additional embodiments optionally further include implantation of a device or composition that comprises platelet-rich plasma (PRP) and/or an anti-Stabilin-2 antibody in conjunction with the HMW-HA.

In some embodiments, an implanted stent comprises a coating of HMW-HA, a filling of HMW-HA, or has portions of the stent wall removed though which HMW-HA can flow from the stent into the surrounding tissue. In additional embodiments, an implanted stent is placed immediately adjacent to the treatment. In other embodiments, an implanted stent is placed further from the treatment area but in a way that allows for direct administration through a branch of the circulatory system. For example, for the treatment or prevention of acute pancreatitis, the stent can be placed in an arterial branch that feeds directly into the pancreas, i.e., the pancreaticoduodenal artery, splenic artery, gastroduodenal artery, or superior mesenteric artery.

In further embodiments, implantation comprises the use of HMW-HA based nanoparticles in the form of organic (e.g., liposome, polymer-based, and dendrimer) particles, inorganic (e.g., gold, carbon-based, mesoporous silica, magnetic, and quantum dot) particles, or hybrid (e.g., liposome-silica, chitosan-carbon, and cell membrane-coated) particles. These particles may then be injected into or proximal to the treatment area. In additional embodiments, the implant is hollow, and the contemplated composition is a gel, liquid, serum, hydrogel, or powder that fills the empty space in the implant for release into the surrounding tissue or bloodstream once placed in the target treatment area.

With respect to suitable HA formulations, it is generally preferred that the HA is of high molecular weight, typically with a molecular weight of between 1,000 kDa and 3,000 kDa. Moreover, the HMW-HA may be crosslinked (e.g., via urea), branched, or linear. While not limiting to the inventive subject matter, the HMW-HA is administered directly into or proximal to the pancreas, preferably through injection or implantation. With respect to suitable dosages, it is generally preferred that the HMW-HA administration is 100 mg to 300 mg per dose, or between 300 mg to 600 mg per dose, or between 600 mg to 1,000 mg per dose, or between 1,000 mg to 3,000 mg per dose, or between 3,000 mg to 5,000 mg per dose, or even higher. The person of ordinary skill in the art will be readily able to determine the proper dosage based on known uses of injectable or implantable HMW-HA and severity of the condition of the patient.

In addition, it is also contemplated that inhibitors of hyaluronidase may be administered to the patient to reduce the degradation of HMW-HA. For example, contemplated inhibitors include L-Ascorbic Acid 6-Hexadecanoate, high molecular mass poly (styrene-4-sulfonate), fenoprofen, gossypol, sodium aurothiomalate, glycerrhizic acid, fatty acids, plant-derived compounds, heparin, and O-sulfated HA (sHA). In some embodiments, other compounds that are unrelated to the function of hyaluronidase may also be administered. For example, contemplated compounds include an anti-inflammatory drug, an antibiotic, and/or an antineoplastic compound. In some embodiments, the HMW-HA will comprise at least 5%, at least 10%, at least 25%, at least 45%, at least 70%, or at least 90% of the total composition administered for treatment. As will be readily appreciated, such inhibitors can be co-administered in the same formulation, and/or separately administered using the same or different route.

In one example, PRP and/or an anti-Stabilin-2 antibody is administered in conjunction with HMW-HA such that the benefits associated with the treatment or prevention of acute pancreatitis and/or other M1 macrophage-driven inflammatory conditions are enhanced as compared to administration of only HMW-HA. In some embodiments, the individual dosage of PRP or an anti-Stabilin-2 antibody is varied per administration, according to a health care provider's discretion, to achieve alternate effects in response to an evolving condition.

With respect to suitable dosages, it is generally preferred that the PRP administration is 100 mg to 300 mg per dose, or between 300 mg to 600 mg per dose, or between 600 mg to 1,000 mg per dose, or between 1,000 mg to 3,000 mg per dose, or between 3,000 mg to 5,000 mg per dose, or even higher. In some embodiments, PRP will be at least 5%, at least 10%, at least 25%, at least 45%, at least 70%, or at least 90% of the total composition administered for treatment. Furthermore, it is generally preferred that the anti-Stabilin-2 antibody administration is 1 mg to 30 mg per dose, or between 30 mg to 300 mg per dose, or between 300 mg to 600 mg per dose, or between 600 mg to 1,000 mg per dose, or between 1,000 mg to 3,000 mg per dose, or between 3,000 mg to 5,000 mg per dose, or even higher.

Most typically, the compositions that treat or prevent acute pancreatitis, or other M1 macrophage-driven inflammatory conditions, will be administered in known and generally acceptable dosage levels contemplated for the composition. For example, suitable dosage levels may typically be between 10-100 mg, or between 100-200, or between 200-600, or between 600-1,000, and even higher. In some embodiments, the administrated dosage may be higher, such as between 200-400 mg/day, or between 400-800 mg/day, or between 800-1,500 mg/day, and even higher.

As related to acute pancreatitis, initial administration is preferably performed between 0 and 7 days of diagnosis by a licensed health care professional of the acute pancreatitis. Similarly, as related to M1 macrophage-driven inflammatory conditions, initial administration is preferably performed between 0 and 7 days of the diagnosis of the condition by a licensed health care professional. In some embodiments, administration of the inventive subject matter is repeated at least one time, at least two times, at least three times, etc., over a treatment period. Consequently, a treatment period is of varying length including at least one day, or at least one week, or at least one month, or at least six months, or at least one year, or at least two years, etc., preferably for a period of at least one month, or at least six months, or at least one year.

As used herein, the term "administering" a pharmaceutical composition or drug refers to both direct and indirect administration of the pharmaceutical composition or drug, wherein direct administration of the pharmaceutical composition or drug is typically performed by a health care professional (e.g., physician, nurse, etc.), and wherein indirect administration includes a step of providing or making available the pharmaceutical composition or drug to the health care professional for direct administration (e.g., via injection, infusion, oral delivery, topical delivery, etc.). It should further be noted that the terms "prognosing" or "predicting" a condition, a susceptibility for development of a disease, or a response to an intended treatment is meant to cover the act of predicting or the prediction (but not treatment or diagnosis of) the condition, susceptibility and/or response, including the rate of progression, improvement, and/or duration of the condition in a subject.

The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided with respect to certain embodiments herein is intended merely to better illuminate the full scope of the present disclosure and does not pose a limitation on the scope of the invention otherwise claimed. No language in the specification should be construed as indicating any non-claimed element essential to the practice of the claimed invention.

It should be apparent to those skilled in the art that many more modifications besides those already described are possible without departing from the full scope of the concepts disclosed herein. The disclosed subject matter, therefore, is not to be restricted except in the scope of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

What is claimed is:

1. A method of treatment of acute pancreatitis in a subject, comprising:
   diagnosing that the acute pancreatitis is an M1 macrophage-driven inflammatory condition; and
   within 7 days after diagnosis, parenterally administering to the subject a composition comprising a high molecular weight hyaluronic acid (HMW-HA) having a molecular weight of at least 1,000 kDa, and optionally further comprising platelet-rich plasma (PRP) and/or an anti-Stabilin-2 antibody,
   wherein the composition is administered in an amount that induces M2 macrophage polarization and/or suppresses M1 macrophage activity.

2. The method of claim 1, wherein the diagnosing comprises ascertaining in the subject a clinically elevated M1 macrophage cell count.

3. The method of claim 1, wherein the parenteral administration of the composition is performed within 3 to 5 days after diagnosis.

4. The method of claim 1, wherein the parenteral administration comprises injection of the composition into or proximal to a treatment area.

5. The method of claim 1, wherein the parenteral administration comprises implantation of the composition or a device comprising the composition into or proximal to a treatment area.

6. The method of claim 1, wherein the parenteral administration is repeated at least three times over a treatment period.

7. The method of claim 1, wherein the amount is an amount that induces M2 macrophage polarization and suppresses M1 macrophage activity.

8. The method of claim 1, wherein the amount is an amount that reduces elevated M1 macrophage cell count and/or that abrogates a cytokine storm.

9. The method of claim 1, wherein the HMW-HA has a molecular weight of between 1,000 and 3,000 kDa.

10. The method of claim 1, wherein the composition further comprises the anti-Stabilin-2 antibody.

11. The method of claim 1, wherein the composition further comprises an anti-inflammatory drug, an antibiotic, and/or an antineoplastic compound.

* * * * *